(12) United States Patent
Burgess

(10) Patent No.: US 11,615,870 B2
(45) Date of Patent: Mar. 28, 2023

(54) SYSTEM AND METHOD FOR FORMAT-AGNOSTIC DOCUMENT INGESTION

(71) Applicant: Rivia Health Inc., Phoenix, AZ (US)

(72) Inventor: Harlow Burgess, Chandler, AZ (US)

(73) Assignee: Rivia Health Inc., Phoenix, AZ (US)

( * ) Notice: Subject to any disclaimer, the term of this patent is extended or adjusted under 35 U.S.C. 154(b) by 457 days.

(21) Appl. No.: 16/775,051

(22) Filed: Jan. 28, 2020

(65) Prior Publication Data

US 2020/0242350 A1 Jul. 30, 2020

Related U.S. Application Data

(60) Provisional application No. 62/797,710, filed on Jan. 28, 2019.

(51) Int. Cl.
*G06F 17/10* (2006.01)
*G16H 10/60* (2018.01)
(Continued)

(52) U.S. Cl.
CPC ............. *G16H 10/60* (2018.01); *G06F 16/22* (2019.01); *G06F 16/243* (2019.01); *G06F 16/93* (2019.01);
(Continued)

(58) Field of Classification Search
CPC ....... G16H 10/60; G06F 16/22; G06F 16/243; G06F 16/93; G06F 40/279; G06F 40/205;
(Continued)

(56) References Cited

U.S. PATENT DOCUMENTS 4,974,260 A * 11/1990 Rudak ................. G06V 10/987
382/311
5,034,985 A * 7/1991 Keough .................... B07C 1/00
382/101
(Continued)

FOREIGN PATENT DOCUMENTS

CA 2836220 A1 * 8/2010 ........... G06F 17/278
CA 3072045 A1 * 2/2019 ............... A01B 3/02
(Continued)

*Primary Examiner* — Shahid K Khan
(74) *Attorney, Agent, or Firm* — Rodney J. Fuller; Booth Udall Fuller, PLC

(57) ABSTRACT

A system for format-agnostic document ingestion including a document ingestion server and a database is disclosed. The server is configured to receive an image of a document comprising text in an unknown format, convert the image, using OCR, into a plurality of text elements a content, a size, and an absolute position. The server is also configured to retrieve data detectors from the database, each associated with a data type anticipated to be in the document, and comprising at least one identifier and direction, and at least one validation criteria. The server is also configured to identify a potential descriptor by comparing the content of each text element with the at least one identifier, and then determine if the text element pointed to by the data detector meets the validation criteria. Finally, the server is configured to associate the validated text element with the data detector, and store the content.

18 Claims, 6 Drawing Sheets

(51) Int. Cl.
*G06F 16/242* (2019.01)
*G06F 16/22* (2019.01)
*G06F 16/93* (2019.01)
*G06N 20/00* (2019.01)
*G06F 40/279* (2020.01)
*G06K 9/62* (2022.01)
*G06V 30/412* (2022.01)
*G06V 30/413* (2022.01)
*G06V 30/414* (2022.01)
*G06V 30/416* (2022.01)
*G06V 30/10* (2022.01)

(52) U.S. Cl.
CPC ......... *G06F 40/279* (2020.01); *G06K 9/6262* (2013.01); *G06N 20/00* (2019.01); *G06V 30/412* (2022.01); *G06V 30/413* (2022.01); *G06V 30/414* (2022.01); *G06V 30/416* (2022.01); *G06V 30/10* (2022.01)

(58) Field of Classification Search
CPC .... G06F 40/295; G06K 9/6262; G06N 20/00; G06V 30/412; G06V 30/413; G06V 30/414; G06V 30/416; G06V 30/10; G06V 30/40
See application file for complete search history.

(56) References Cited

U.S. PATENT DOCUMENTS

| | | | | |
|---|---|---|---|---|
| 5,387,783 A * | 2/1995 | Mihm | ................ | G06Q 99/00 235/375 |
| 5,875,428 A * | 2/1999 | Kurzweil | ............ | G09B 17/003 704/260 |
| 8,595,235 B1 * | 11/2013 | Sampson | ............... | G06V 10/75 707/758 |
| 9,483,455 B1 * | 11/2016 | Bastide | ................ | G06F 16/148 |
| 10,853,567 B2 * | 12/2020 | Hegde | ............... | G06F 40/186 |
| 2003/0225527 A1 * | 12/2003 | Antonysamy | .......... | G16B 20/00 702/19 |
| 2005/0076013 A1 * | 4/2005 | Hilbert | ................... | G06Q 10/10 |
| 2005/0289182 A1 * | 12/2005 | Pandian | ................. | G06Q 10/10 |
| 2009/0006394 A1 * | 1/2009 | Snapp | ................. | G06F 16/2468 |
| 2009/0074291 A1 * | 3/2009 | Iinuma | ................. | G06V 30/413 382/178 |
| 2009/0144319 A1 * | 6/2009 | Panwar | .................... | G06F 16/25 707/999.102 |
| 2010/0161616 A1 * | 6/2010 | Mitchell | ................ | G06F 16/31 707/741 |
| 2010/0211533 A1 * | 8/2010 | Yang | ..................... | G06F 16/958 706/12 |
| 2010/0329555 A1 * | 12/2010 | Chapman | ............. | G06V 30/127 382/167 |
| 2011/0182422 A1 * | 7/2011 | Anderson | ........... | G06F 16/5866 380/28 |
| 2013/0041909 A1 * | 2/2013 | Coleman | ............... | H04L 63/102 707/758 |
| 2014/0122264 A1 * | 5/2014 | Gebhart | ................. | G06Q 40/10 705/16 |
| 2014/0195891 A1 * | 7/2014 | Venkata Radha Krishna Rao | ...... | G06F 40/117 715/234 |
| 2014/0369602 A1 * | 12/2014 | Meier | .................. | G06V 30/412 382/182 |
| 2015/0220518 A1 * | 8/2015 | Le Chevalier | .......... | G06F 16/93 707/741 |
| 2016/0350950 A1 * | 12/2016 | Ritchie | .................. | G06F 40/18 |
| 2018/0239959 A1 * | 8/2018 | Bui | ....................... | G06Q 10/10 |
| 2018/0341688 A1 * | 11/2018 | Ganesh | ............... | G06F 16/2465 |
| 2018/0350144 A1 * | 12/2018 | Rathod | ................. | H04W 4/021 |
| 2019/0102620 A1 * | 4/2019 | Siddiq | ............... | G06F 16/24575 |
| 2019/0171704 A1 * | 6/2019 | Buisson | ............... | G06F 40/131 |
| 2019/0278853 A1 * | 9/2019 | Chen | .................. | G06F 16/211 |
| 2019/0303663 A1 * | 10/2019 | Krishnapura Subbaraya | ............. | G06V 30/414 |
| 2020/0134368 A1 * | 4/2020 | Chopra | .................. | G06N 5/003 |
| 2021/0012103 A1 * | 1/2021 | Bassu | ..................... | G06F 16/84 |

FOREIGN PATENT DOCUMENTS

| | | | | |
|---|---|---|---|---|
| EP | 1965309 A1 * | 9/2008 | ............ | G06F 17/211 |
| WO | WO-9641275 A1 * | 12/1996 | ............ | G06F 19/00 |
| WO | WO-2018125264 A1 * | 7/2018 | ......... | G06F 11/3495 |

* cited by examiner

US 11,615,870 B2

SYSTEM AND METHOD FOR FORMAT-AGNOSTIC DOCUMENT INGESTION

RELATED APPLICATIONS

This application claims the benefit of U.S. provisional patent application 62/797,710, filed Jan. 28, 2019 titled "System and Method for Medical Bill Management," the entirety of the disclosure of which is hereby incorporated by this reference.

TECHNICAL FIELD

Aspects of this document relate generally to format-agnostic document ingestion.

BACKGROUND

Although there is increasing interest in moving various workflows and processes to be entirely electronic, a great deal of interactions between companies and individuals involves human-readable documents, either "analog" (e.g. paper documents) or digital (e.g. PDF documents). Even among documents of the same type, such as shipping manifests for freight delivery services, each party will execute that task in a slightly different manner, resulting in everyone having a different document format.

This has been a long-standing problem, and is one that complicates efforts to ingest a large number of documents, whether to digitize old physical records or to gather documents from various sources. While these tasks may be accomplished manually on a small scale, those methods do not scale well, and quickly get bogged down when trying to coordinate multiple document formats.

Conventional solutions to this problem have relied on systems that understand the various document formats. However, these conventional systems require training, and are fragile. A small change in document format through such systems into chaos. While slightly more scalable than manual effort, conventional solutions require a level of preparation and upkeep that often negates most of the efficiency of the automation.

SUMMARY

According to one aspect, a system for format-agnostic document ingestion includes a document ingestion server having a processor and a memory, the document ingestion server communicatively coupled to a database, and the processor configured to receive an image of a document, the document including text arranged in an unknown format. The processor is also configured to convert, using optical character recognition, the image of the document into a plurality of text elements, each text element including a content, a size, and an absolute position within the document. The processor is also configured to identify a document type by searching the content of each text element for a plurality of distinguishing strings, each distinguishing string being unique to one document type, as well as retrieve a plurality of data detectors from the database based on the document type, each data detector associated with a data type that is anticipated to be in the document. Each data detector includes at least one identifier that is one of a potential label and a potential format, at least one direction describing a potential relative direction of a text element having a label associated with the data detector, and at least one validation criteria. Each validation criteria describes one of a valid format and a valid range. The processor is configured to determine a source of the document by comparing the at least one identifier of a data detector associated with a data type that is unique among potential document sources with the content of each text element of the plurality of text elements. The processor is configured to, for each data detector, order at least one of the identifiers and the directions according to a history stored in the database and associated with the source, and identify a table within the document by calculating for each text element of the plurality of text elements a relative position of at least one neighboring text element relative to the text element using the absolute position of the text element, and comparing the relative positions of the plurality of text elements. Furthermore, the processor is configured to locate a header for the table by comparing the content of the text elements within the table with the identifiers of the plurality of data detectors and then identifying the data type of the matching text elements, the header being one of a row and a column, and validate, for each identified text element in the header, at least one text element within the other of a row and a column described by the identified text element in the header with the validation criteria of the data detector that identified the identified text element in the header. The processor is configured to also associate, for each identified text element in the header, at least one validated text element within the other of the row and the column described by the identified text element in the header with the data detector that identified the identified text element in the header, and identify a potential descriptor by comparing the content of each text element not part of the table with the at least one identifier of at least one data detector. The processor is also configured to determine if the text element pointed to by one of the at least one direction of the data detector used to identify the potential descriptor meets the validation criteria of the data detector, associate the validated text element with the data detector, and store, for each text element associated with one data detector of the plurality of data detector, the content of the text element, in the database. Lastly, the processor is configured to update, for each data detector, the history associated with the source, according to which identifier of the at least one identifier and which direction of the at least one direction matched the most text elements of the data type described by the data detector in the document.

Particular embodiments may comprise one or more of the following features. The processor may be further configured to train a machine learning model correlating text elements with the data detectors they have been associated with, determine whether the machine learning model performs better than one or more data detectors, and/or automatically employ the machine learning model in place of the one or more data detectors once the machine learning model outperforms the one or more data detectors. Determining the source of the document may include identifying all postal addresses in the document based upon an observed format, validating each postal address, placing each postal address in a standard format, and/or comparing each address with a list of addresses unique to each of a plurality of known document sources. Each text element may further include a size. The potential format of each data detector may further include a potential size.

According to another aspect of the disclosure, a system for format-agnostic document ingestion, includes a document ingestion server having a processor and a memory. The document ingestion server is communicatively coupled to a database, the processor configured to receive an image of a document, the document including text arranged in an unknown format. The processor is also configured to convert, using optical character recognition, the image of the document into a plurality of text elements, each text element having a content, a size, and an absolute position within the document. The processor is also configured to retrieve a plurality of data detectors from the database, each data detector associated with a data type that is anticipated to be in the document. Each data detector includes at least one identifier that is a potential label, at least one direction describing a potential relative direction of a text element having a label associated with the data detector, and at least one validation criteria. Each validation criteria describes a valid format. The processor is further configured to identify a potential descriptor by comparing the content of each text element with the at least one identifier of at least one data detector, and determine if the text element pointed to by one of the at least one direction of the data detector used to identify the potential descriptor meets the validation criteria of the data detector, and associate the validated text element with the data detector. Finally, the processor is configured to store, for each text element associated with one data detector of the plurality of data detector, the content of the text element, in the database.

Particular embodiments may comprise one or more of the following features. The processor may be further configured to identify a document type by searching the content of each text element for a plurality of distinguishing strings. Each distinguishing string may be unique to one document type. The plurality of data detectors retrieved from the database may be selected based on the document type. Each identifier may be at least one of a potential label and a potential format. Each validation criteria may describe at least one of a valid format and a valid range. The processor may be further configured to determine a source of the document by comparing the at least one identifier of a data detector associated with a data type that may be unique among potential document sources with the content of each text element of the plurality of text elements, and, for each data detector, may order at least one of the identifiers and the directions according to a history stored in the database and associated with the source. The processor may be further configured to update, for each data detector, the history associated with the source, according to which identifier of the at least one identifier and which direction of the at least one direction matched the most text elements of the data type described by the data detector in the document. The processor may be further configured to identify a table within the document by calculating for each text element of the plurality of text elements a relative position of at least one neighboring text element relative to the text element using the absolute position of the text element, and/or comparing the relative positions of the plurality of text elements. The processor may be configured to locate a header for the table by comparing the content of the text elements within the table with the identifiers of the plurality of data detectors and then identifying the data type of the matching text elements. The header may be one of a row and a column. The processor may be configured to validate, for each identified text element in the header, at least one text element within the other of a row and a column described by the identified text element in the header with the validation criteria of the data detector that identified the identified text element in the header. Lastly, the processor may be configured to associate, for each identified text element in the header, at least one validated text element within the other of the row and the column described by the identified text element in the header with the data detector that identified the identified text element in the header.

According to yet another aspect of the disclosure, a method for format-agnostic document ingestion includes receiving, by a processor, an image of a document, the document having text arranged in an unknown format. The method also includes converting, using optical character recognition performed by the processor, the image of the document into a plurality of text elements, each text element having a content, a size, and an absolute position within the document. The method further includes retrieving a plurality of data detectors, each data detector associated with a data type that is anticipated to be in the document, each data detector having at least one identifier that is a potential label, at least one direction describing a potential relative direction of a text element having a label associated with the data detector, and at least one validation criteria. Each validation criteria describes a valid format. The method includes identifying a potential descriptor by comparing the content of each text element with the at least one identifier of at least one data detector, determining if the text element pointed to by one of the at least one direction of the data detector used to identify the potential descriptor meets the validation criteria of the data detector, and associating the validated text element with the data detector. Finally, the method includes storing, for each text element associated with one data detector of the plurality of data detector, the content of the text element.

Particular embodiments may comprise one or more of the following features. The method may also include identifying a document type by searching the content of each text element for a plurality of distinguishing strings, each distinguishing string being unique to one document type. The plurality of data detectors retrieved may be selected based on the document type. Each identifier may be one of a potential label and a potential format. Each validation criteria may describe one of a valid format and a valid range. The method may further include determining a source of the document by comparing the at least one identifier of a data detector associated with a data type that may be unique among potential document sources with the content of each text element of the plurality of text elements. The method may also include ordering, for each data detector, at least one of the identifiers and the directions according to a history associated with the source, and updating, for each data detector, the history associated with the source, according to which identifier of the at least one identifier and which direction of the at least one direction matched the most text elements of the data type described by the data detector in the document. The method may also include identifying a table within the document by calculating for each text element of the plurality of text elements a relative position of at least one neighboring text element relative to the text element using the absolute position of the text element, and comparing the relative positions of the plurality of text elements. The method may further include locating a header for the table by comparing the content of the text elements within the table with the identifiers of the plurality of data detectors and then identifying the data type of the matching text elements. The header may be one of a row and a column. The method may include validating, for each identified text element in the header, at least one text element within the other of a row and a column described by the identified text element in the header with the validation criteria of the data detector that identified the identified text element in the header, and associating, for each identified text element in the header, at least one validated text element within the other of the row and the column described by the identified text element in the header with the data detector that identified the identified text element in the header. The method may also include training a machine learning model correlating text elements with the data detectors they have been associated with, and/or determining whether the machine learning model performs better than one or more data detectors, and/or automatically employ the machine learning model in place of the one or more data detectors once the machine learning model outperforms the one or more data detectors. Determining the source of the document may include identifying all postal addresses in the document based upon an observed format, validating each postal address, placing each postal address in a standard format, and/or comparing each address with a list of addresses unique to each of a plurality of known document sources.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

Figure 1:
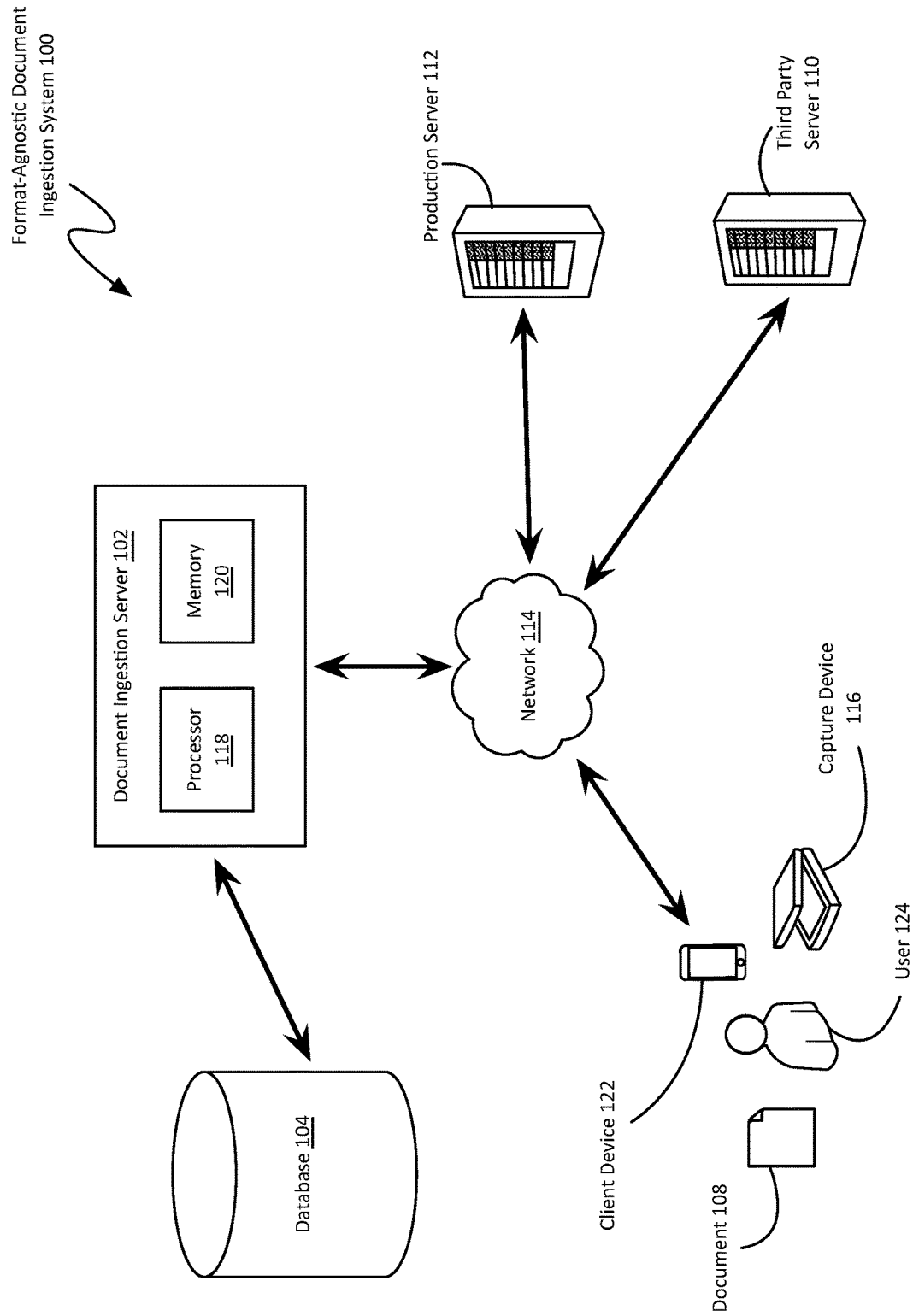
FIG. 1 is a network view of a format-agnostic document ingestion system.

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as "an example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

Although there is increasing interest in moving various workflows and processes to be entirely electronic, a great deal of interactions between companies and individuals involves human-readable documents, either "analog" (e.g.

paper documents) or digital (e.g. PDF documents). Even among documents of the same type, such as shipping manifests for freight delivery services, each party will execute that task in a slightly different manner, resulting in everyone having a different document format.

This has been a long standing problem, and is one that complicates efforts to ingest a large number of documents, whether to digitize old physical records or to gather documents from various sources. While these tasks may be accomplished manually on a small scale, those methods do not scale well, and quickly get bogged down when trying to coordinate multiple document formats.

Conventional solutions to this problem have relied on systems that understand the various document formats. However, these conventional systems require training, and are fragile. A small change in document format throw such systems into chaos. While slightly more scalable than manual effort, conventional solutions require a level of preparation and upkeep that often negates most of the efficiency of the automation.

Contemplated herein is a system and method for format-agnostic document ingestion. The ability to ingest documents independent of how they are formatted allows the automation and/or scaling of processes that previously had to be done manually, or automated only after great expense, time, and effort from humans.

Advantageous over conventional systems and methods, the format-agnostic document ingestion systems and methods contemplated herein are able to operate without needing to know how the documents are formatted. Conventional systems must rely on either manual entry of these documents, or fragile automated systems that must be manually taught every new document format. Format updates can require conventional systems to stop operating while the new format is trained. The systems contemplated herein are able to continue operating, even through many rapid format changes.

The format-agnostic document ingestion systems and methods contemplated herein facilitate the interaction of two organizations, each of whom may have a particular way of communicating and storing data. Removing the formatting to documents from the mix allows these organizations to work cooperatively without having to alter their own systems or workflows, which are often built up over a long time span, at great cost. Conventional systems created to facilitate these interactions would need to be configured for the particular needs and methods of the organizations; any change on either end would require more configuration. The systems and methods contemplated herein can accomplish the task with greater efficiency, little to no initial configuration, and even less configuration to deal with format changes. Additional use cases will be discussed, below.

In the context of the present description and the claims that follow, format-agnostic means the system is able to extract desired textual data from a document independent of how that data is organized within the document, how it is labeled (e.g. how it is described, where the labels are with respect to the information, etc.), or how it is displayed. Furthermore, in the context of the present description and the claims that follow, ingestion refers to the capture of information from a document, placing it in an electronic form that increases its utility (e.g. placement into a universally recognized data format, making paper records digital, etc.).

It should be noted that, while the discussion of systems and methods below will mainly be done in the context of ingesting a paper document presented to the system as an image, these systems and methods may be applied to documents existing in a wide range of states. For example, in some embodiments, the system may receive a document that is electronic in form, but has been formatted for human consumption (e.g. a formatted PDF of an invoice, etc.). As another example, a document may be provided to the system in an electronic machine-readable form (e.g. a database record, CSV file, etc.), but makes use of an unknown labeling or organizational method (e.g. some people organize a set of data in rows, while others do it in columns, etc.). Additional examples will be provided below.

FIG. 1 is a network view of a non-limiting example of a format-agnostic document ingestion system 100. As shown, the system 100 comprises a document ingestion server 102. Going forward, reference is made to a user 124 of the system 100. In the context of the present description and the claims that follow, a user 124 is an individual interfacing or interacting with the system 100. They have access to the system and are able to perform the same operations as a corporate third party who may interact with the server 102 over a network 114.

As shown, the system 100 includes a document ingestion server 102 having a processor 118 and a memory 120. The server 102 is responsible for collecting the documents 108 (e.g. bills, invoices, review, etc.). In some embodiments, the server 102 may be a discrete piece of hardware, while in others it may be a distributed computing environment spread across multiple machines. In some embodiments, the server 102 may be implemented in a cloud environment (e.g. the functionality described may be provided in an instantiated environment implemented on remote hardware, etc.). In other embodiments the system 102 may operate remotely and be offered over the network as a software-as-a-service (SAAS).

In some embodiments, the server 102 may be communicatively coupled to a database 104 through a network 114, the database 104 also a part of the system 100. In some embodiments, the database 104 may be localized with (e.g. internal to, etc.) the server 102. In other embodiments, the database 104 may be distinct from the server 102. In still other embodiments, the database 104 may be remote to the server 102 (e.g. executed in a cloud environment, etc.). The database 104 may be use to store various information used by the system 100, including but not limited to user profiles and preferences, bills, explanation of benefits, financial records, payment methods, payment histories, biographical information, and the like. The database 104 may be implemented in any architecture known in the art, such as SQL, NoSQL, and the like. It should be noted that there are also embodiments where the system 100 does not have a database 104, and all of the storage and retrieval operations discussed below are performed in the memory 120 of the server 102.

Users 124 may interact with the server 102 through a client device 122 (e.g. phone, tablet, laptop computer, desktop computer, etc.). According to various embodiments, the user-server interaction may be accomplished through various interfaces, including but not limited to, a web portal, a specialized app or application, and the like.

Figure 4:
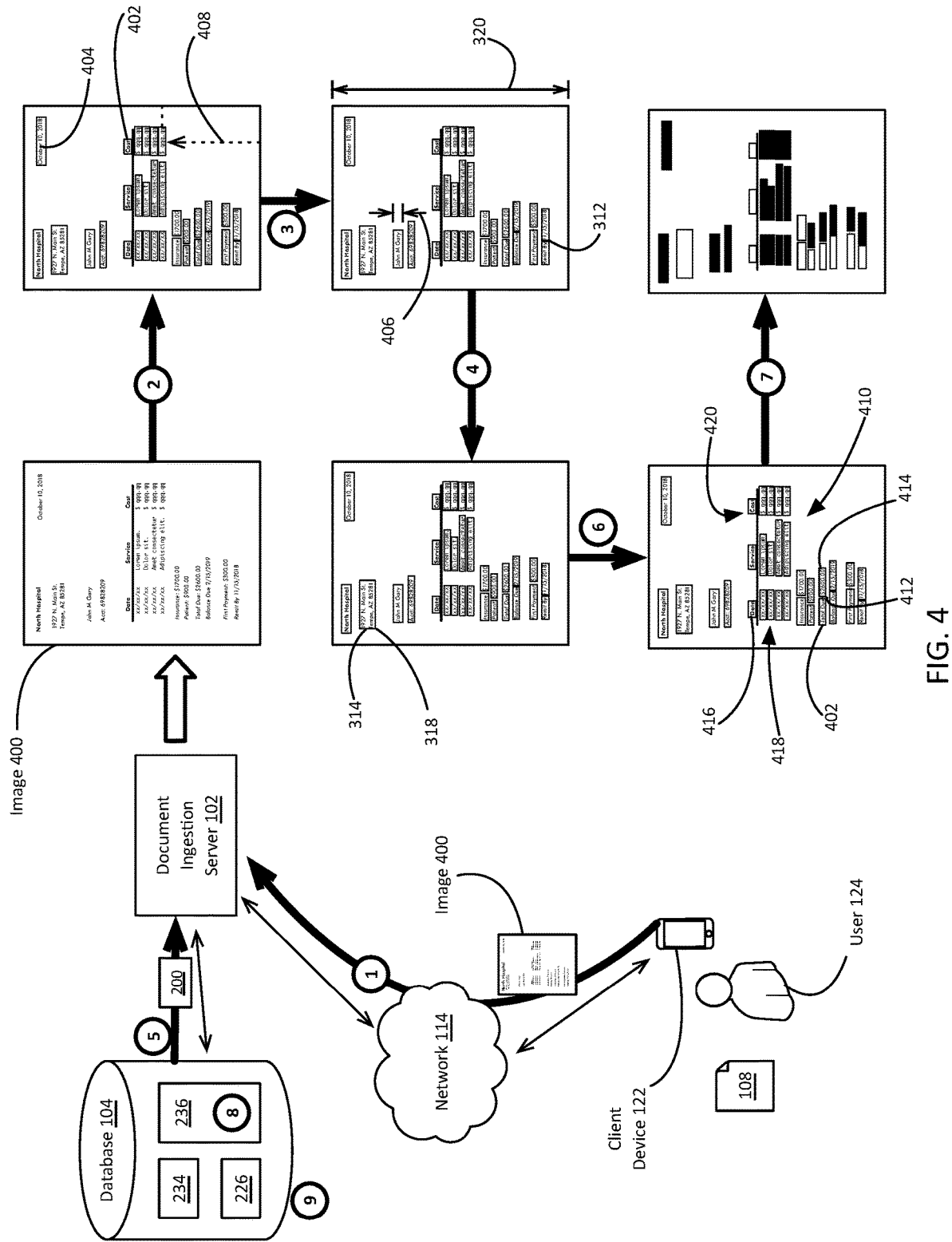
FIG. 4 is a schematic flow for document ingestion using a format-agnostic document ingestion system.

According to various embodiments, a document 108 may be submitted to the server 102 in the form of an image (see image 400 of FIG. 4). In some embodiments, a user 124 may submit a document 108 by capturing an image 400 using a camera on their client device 122 (e.g. smartphone, etc.). In other embodiments, the document 108 may be captured using a capture device 116. In the context of the present description and the claims that follow, a capture device 116 is an imaging device that is designed for imaging documents. Examples include, but are not limited to, flatbed scanners, sheet-fed scanners, book scanners, and the like.

According to various embodiments, the server 102 may receive some electronic representation of the document 108 through one or more channels. In some embodiments, an image 400 may be submitted to the server 102 through an application interface. As a specific example, in one embodiment, a user 124 may capture an image 400 of the document 108 using the camera on their smartphone client device 122, and thereafter submit it to the server 102 using an app loaded on the phone.

In other embodiments, electronic documents may be sent to the server 102 using the same channels they were received through. For example, in one embodiment, an electronic document 108 received by a user 124 in an email message may be submitted to the server 102 by simply forwarding the email. As an option, the system 100 may provide the user 124 an email address that is unique to them, to which they can send items for ingestion and association with them or an entity they represent. In still other embodiments, the server 102 may allow for the uploading of documents using authenticated and secure protocols and methods (e.g. FTP, SFTP, etc.) as is known in the art.

In some embodiments, the server 102 may also be configured to interact with one or more production servers 112. In the context of the present description and the claims that follow, a production server 112 is a server that is associated with the production of a document 108. In some embodiments, it a server affiliated with the party who produced a document 108, while in others, the production server 112 itself generated the document 108. As will be discussed in greater detail below, it may be advantageous to be able to determine the source of a document 108.

In other embodiments, the server 102 may also communicate with third party servers 110 for interactions that do not involve obtaining a document 108 or returning a results. For example, in some embodiments, the third party server 110 may be contacted to validate some information obtained by the system 102 during the ingestion process (e.g. determine whether an address exists, whether a credit card number is valid, etc.). In other embodiments, the third party server 110 may be used to make a determination based, at least in part, on information obtained from an ingested document.

Figure 2:
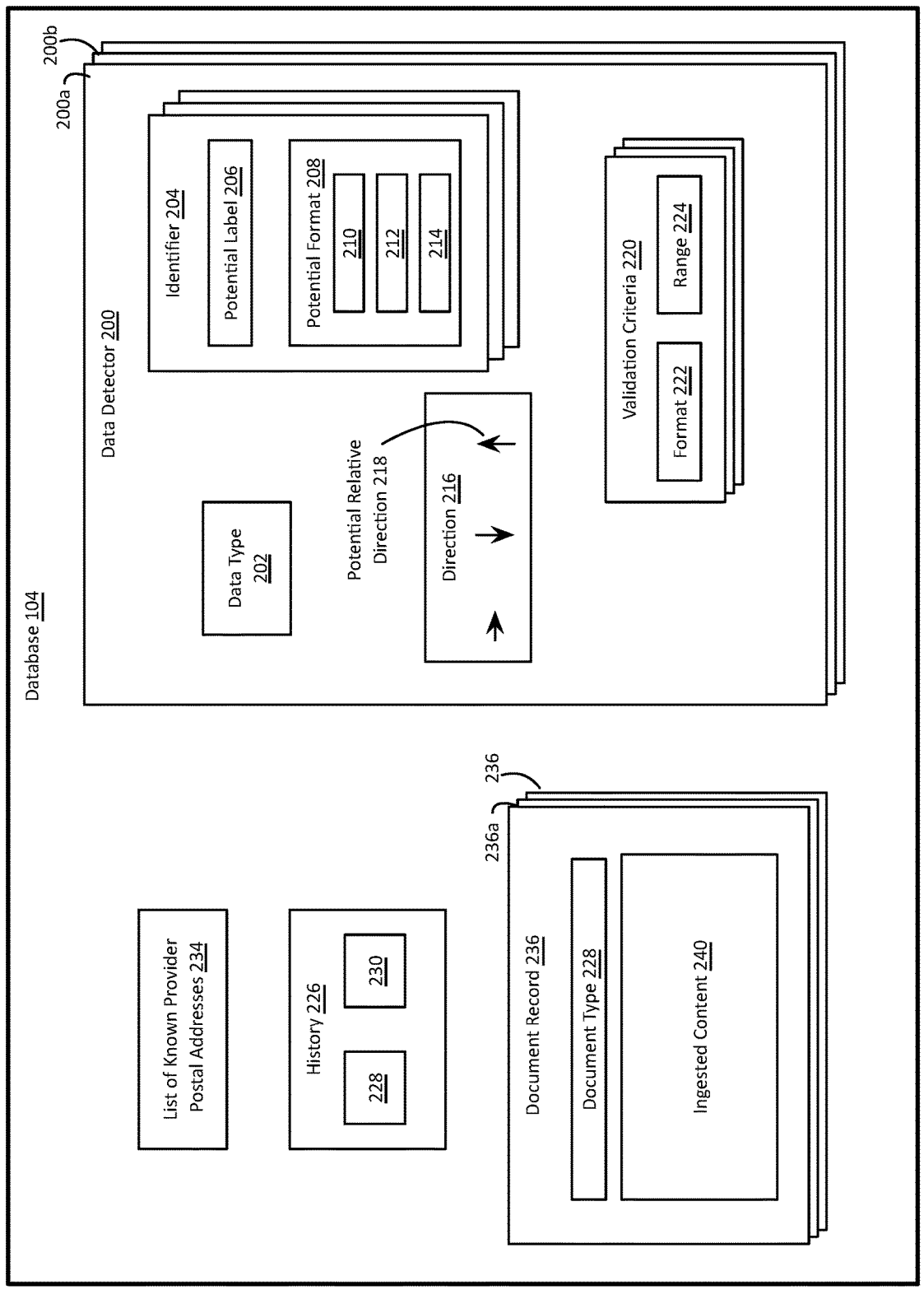
FIG. 2 is a schematic view of the contents of a database belonging to a format-agnostic document ingestion system.

FIG. 2 is a schematic view of a non-limiting example of a database 104 belonging to a format-agnostic document ingestion system 100. As shown, the database 104 may be used to store a variety of information including, but not limited to, document records 236 as well as information used to ingest documents provided by a user 124. It should be noted that the data objects depicted in FIG. 2 are meant to provide context for a discussion of the various pieces of data that the system 100 works with, and is not meant to be limiting or imply the requirement of a particular structure or storage format. Those skilled in the art will recognize that there are numerous ways the following information may be organized, stored, and accessed within a database.

The database 104 may store a plurality of data detectors 200. In the context of the present description and the claims that follow, a data detector 200 is a collection of data that is used to identify and validate particular pieces of information among the text extracted from a document 108.

As shown, each data detector 200 is associated with a data type 202. In the context of the present description and the claims that follow, a data type 202 refers to a specific piece of data (e.g. date of invoice, type of healthcare service rendered, etc.) rather than the species of data (e.g. date, string, etc.).

Each data detector 200 comprises at least one identifier 204, which is a piece of information that can be used to identify an instance of the data type 202 within a document 108. One example of an identifier is a potential label 206, which is a textual indicator identifying a nearby piece of information (e.g. "Payment due", "ID number", etc.).

Another example of an identifier is a potential format 208, meaning a patterning of kinds of data (e.g. a dollar sign followed by numbers and a period and two more numbers to indicate a monetary value, etc.). Examples of potential format 208 identifiers include, but are not limited to, a potential size 210 (e.g. a size of the element relative to the document in which it is found, the absolute size of an element, etc.), a regular expression 212 (e.g. looks for character sequences that match a regular expression defined within the data detector 200 that seeks for particular characters or classes of characters that are arranged in a particular manner, etc.), and a potential font 214.

In some embodiments, a data detector 200 may require the observation of both a label 206 and a format 208, while in others it may be limited to one or the other. In some embodiments, a data detector 200 may have more than one identifier 204, for information that may be labeled in numerous ways. For example, an identification number could have the labels "ID number", "ID No.", "ID", and the like.

As shown, the data detector 200 also comprises at least one direction 216, meaning one or more potential relative directions 218 where a value may be found, with respect to its identifier. For example, a data detector 200 having an potential label 206 of "Statement Date" may include "right" as a direction 216. Those skilled in the art will recognize that relative direction information may be represented in numerous ways, including verbal (e.g. "right", "up", etc.) and numerical (e.g. Cartesian offset, polar coordinates, etc.).

According to various embodiments, the data detector 200 may also include at least one validation criteria 220, which must be satisfied in order to accept a piece of text content as a value being described by the identifier 204. Examples include, but are not limited to, valid formats 222 (e.g. two decimal places for dollar amounts, etc.) and valid ranges 224 (e.g. date of birth within the last 120 years, etc.).

The database 104 also may comprise one or more history records 226. In the context of the present description and the claims that follow, a history 226 is a collection of observations made during previous document ingestion that are specific to a particular document source (e.g. healthcare provider, bank, etc.) and/or particular document type (e.g. bill, receipt, check, credit card, insurance card, manifest, etc.). It should be noted that a history 226 is different than a recording of a particular document format. Instead, it provides a preferred ordering for the various potential relative directions 218 and/or identifiers 204 that may be observed by that data detector 200. For example, in one embodiment, if the first medical bill from North Hospital ingested by the server 102 positioned the dollar value for the total amount due to the right of the "total amount due" label, the history 226 for North Hospital bills would place "right" at the front of a list of possible directions for the data detector 200 for that label. The use of histories 226 is advantageous as it permits optimized operation based on previous documents without locking the system 100 into a particular document format, as is done with conventional systems.

As shown, the database 104 may also comprises a plurality of document records 236, according to some embodiments, each comprising data regarding a particular document 108. It should be noted that said document 108 is not limited to tangible documents ingested into the system, but also electronic, human readable documents (e.g. a PDF of an explanation of benefits, etc.), digital files read for storage in the database 104, and the like.

As shown, according to various embodiments, the document record 236 may comprise a document type 228 (e.g. bill, receipt, manifest, etc.), and other ingested content 240 (e.g. data ingested from the document 108 that has been verified by the user 124 or some other entity or process, etc.). In some embodiments, the information obtained from a processed image 400 may be stored, but the image deleted or downgraded in resolution to preserve storage space. In other embodiments, the image 400 may be stored in the database 104, either as part of the document record 236 or as a separate record linked to the document record 236.

The database 104 may comprise information about various document sources, to facilitate the determination of the source of various documents 108 ingested into the server 102. As will be discussed in greater detail below with respect to FIG. 4, in some embodiments, the database 104 may comprise a list 234 of postal addresses that are unique to known document sources. In other embodiments, additional or alternative identifying information may be stored and used in similar manner.

In some embodiments, the methods discussed thus far may be used as a stepping stone toward automation with artificial intelligence or machine learning. Conventional document management and classification system that use machine learning or artificial intelligence can be effective, but at the cost of painstaking, human-driven training and model refinement. Contemplated herein is a system 100 that not only performs better than conventional systems, it is able to train its own potential replacement.

According to various embodiments, a machine learning model 232 may be trained to correlate text elements (see text elements 402 of FIG. 4) with data detectors 200 they have been associated with by the server 102. Periodically, as this model 232 continues to train while the server 102 ingests more documents, the server 102 determines if the machine learning model 232 performs better than one or more of the data detectors 200 being modeled. If the model performs better, the server 102 may automatically employ the machine learning model 232 in place of the one or more data detectors, once they fall behind in performance.

Figure 3:
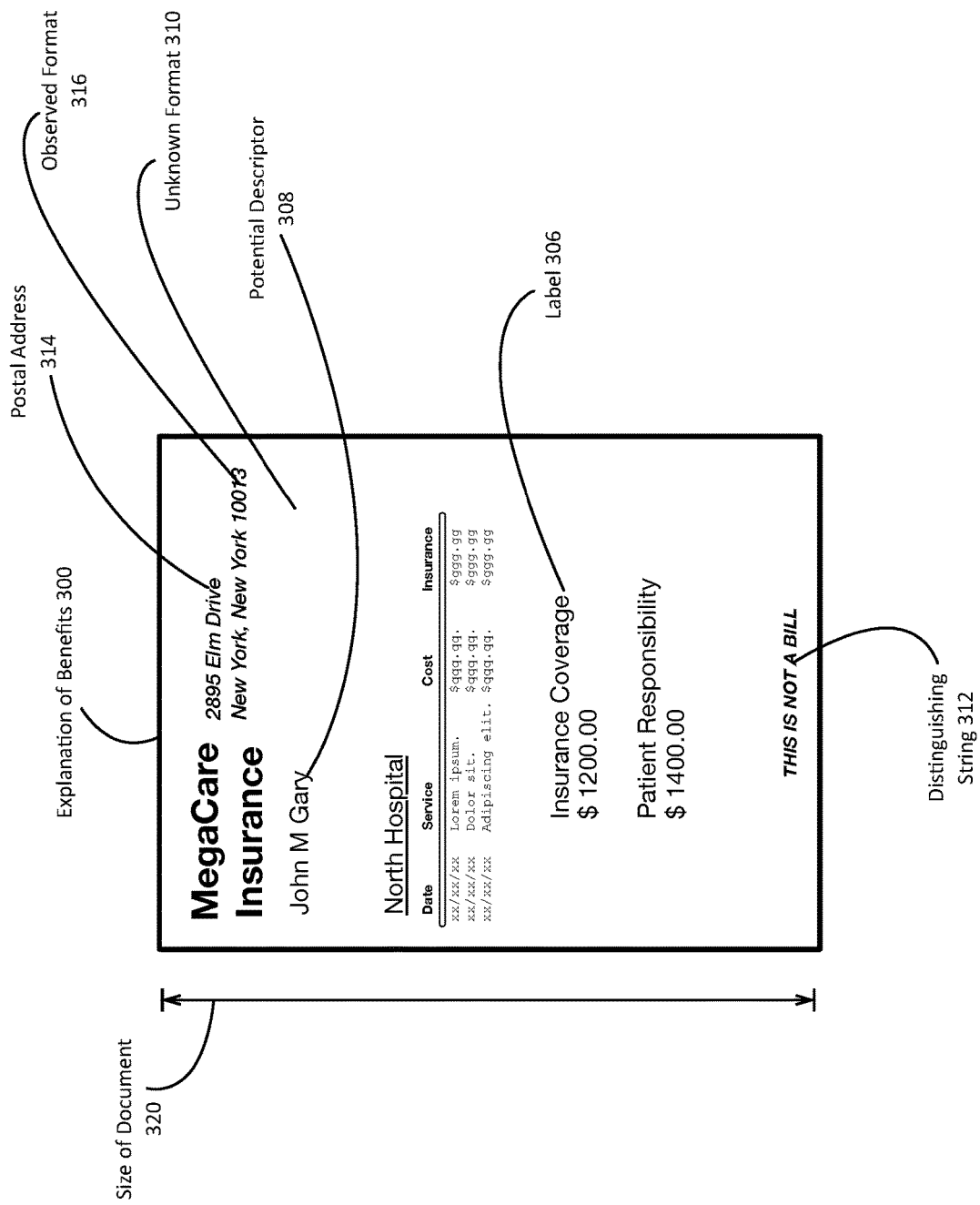
FIG. 3 is a schematic view of an exemplary document.

FIG. 3 is a schematic view of a non-limiting example of a document 108. Specifically, FIG. 3 shows a non-limiting example of a explanation of benefits 300 with an unknown format 310. It should be noted that the use of an explanation of benefits in this non-limiting example is not meant to imply that the systems 100 and methods contemplated herein are bound to any particular industry, or any particular kind of document. These systems and methods may be adapted for use with any document containing information. As will be discussed in greater detail with respect to FIG. 4, each document has information that is identifiable by position and or a label 306. Until a data detector 200 is employed, each piece of text is a potential descriptor 308.

The system 100 is able to distinguish between two or more document types, according to various embodiments. This is particularly beneficial for document types that may otherwise be confused by a user 124. For example, in some embodiments, the system 100 is able to differentiate between an explanation of benefits and a medical bill, which sometimes can look very similar. In some embodiments, the system 100 is able to distinguish between document types by searching for a distinguishing string 312, which is a piece of text that is reliably unique to a particular document type. For example, explanation of benefits often have "This is not a bill" printed on them somewhere.

Many documents have a source 230 identified, indicating where the document 108 came from or who produced it. Many documents also have a postal address 314 for the source 230, provided in an observed postal address format 316.

As shown, an explanation of benefits 300 may include, but is not limited to, patient name, a source 230, a total amount due, a balance due date, a date of service, service details, a statement date, and/or an account number. Explanations of benefits 300 may also include a payment amount and a payment due date, for bills with an established payment plan.

FIG. 4 is a schematic flow for a non-limiting example of document ingestion using a format-agnostic document ingestion system 100. Format-agnostic document ingestion provides an advantage over conventional, rigid format based systems or non-scalable, expensive manual systems. Being format-agnostic allows the system 100 to quickly incorporate documents from previously unknown sources or in previously unknown formats, which is time consuming and costly for conventional systems to deal with. This also allows the system 100 to work with great efficiency, without requiring document sources to make any changes to the way they operate.

It should be noted that this process is intended for ingesting documents 108 that were intended for human consumption. Documents or files that are computer formatted (e.g. data provided as arrays and matrices, some data structure having indisputable relationships between entries rather than contextual relationships on a two dimensional surface, etc.) may be ingested using much more streamlined methods that may include some form of validation and label/format normalization.

First, the system 100 receives an image 400 of a document 108. See circle '1'. The image 400 may be a digital photograph of the document 108 captured with the client device 122, a high resolution scan of the document 108 obtained with the capture device 116, or it may be an electronic version of a human-formatted document (e.g. a PDF of an explanation of benefits, etc.), or some other visual format.

Next, the image 400 is converted into a plurality of text elements 402 using optical character recognition or machine vision to identify what is text. See circle '2'. Characters are grouped together as words and sentences using various attributes that may include, but are not limited to, kerning, spacing, alignment, font, and the like. These groupings are turned into individual text elements 402.

In the context of the present description and the claims that follow, a text element 402 is a data object that comprises a content 404 (e.g. the characters, etc.) and an absolute position 408 of that content within the document (e.g. Cartesian coordinates+page number, etc.). In some embodiments, each text element 402 may also include a size 406 of the text, or other visual attributes.

According to some embodiments, the system 100 determines what type of document 108 is being ingested. See circle '3'. In some embodiments, the document type may be provided by a user 124 when they capture an image of the document 108. In other embodiments, the system 100 may automatically differentiate between two or more possible document types using various methods.

In some embodiments, the system 100 may differentiate between a number of potential document types by searching the content 404 of each text element 402 in the image 400 for at least one distinguishing string 312 that is reliably unique to one particular document type. As a specific example, medical bills from a hospital can sometimes be difficult to distinguish from explanations of benefit from an insurance provider, as they both contain much of the same information. However, the explanation of benefits often includes the words "This is not a bill"; searching for that content 404 may allow the system 100 to determine if the image 400 is a bill or an explanation of benefits.

In some embodiments, the system 100 may determine what kind of document 108 is being ingested using structural features. For example, in one embodiment, the system 100 may use the size 320 of the document 108 to differentiate between a card sized document and a letter sized document. This determination may be made by comparing the size 406 of the text elements 402 with the relative size 320 of the document 108 in the image 400, allowing the system 100 to conclude if the image 400 is of a card or a letter sized document. Other document types may be determined using visual features that are specific and common to that type (e.g. the particular OCR font used to print the serial number along the bottom left corner of a check, etc.).

Next, in some embodiments, the system 100 determines the identity of the document source 230 (e.g. store, insurance company, government, etc.) that created the document 108 being considered. Some embodiments approach this task using postal addresses 314, which have a predictable observed format 316 and are relatively easy to identify.

First, each element 402 is examined to determine if it contains a postal address 314. See circle '4'. After locating an address, it is placed in a standard postal address format 318 to facilitate comparison with a list 234 of addresses unique to known document sources. If the address matches an entry on the list 234, the source 230 has been identified. If none of the addresses found in the image 400 are on the list 234, then the system 100 examines the elements 402 that are closest to the found addresses, seeking the source's name. The name may be identified using various methods, including but not limited to comparison with a list of potential sources, a comparison of size and/or formatting of an element closest to the address with the majority of the other elements (e.g. source name is likely to be visually distinct, etc.), and the like.

Once the document source 230 has been identified, a plurality of data detectors 200 may be retrieved from the database 104. See circle '5'. The data detectors 200 are selected based on the data types 202 that are anticipated to be in the document, and may also be chosen based, at least in part, on the document type (e.g. a first plurality of data detectors 200a may be chosen for an order form and a second plurality of data detectors 200b may be chosen for an invoice, etc.).

In some embodiments, a history 226 specific to that source 230 may also be retrieved from the database 104. Using the history 226, one or more data detectors 200 may be configured, which includes but is not limited to changing the order of the various identifiers 204 and/or directions 216 to reflect the previous observations, as was discussed above.

Once the data detectors 200 have been retrieved and configured, the content of the document 108 may be ingested. In some embodiments, the system 100 may begin with the ingestion of any tables 410 in the document. See circle '6'.

According to various embodiments, a table 410 is identified by calculating, for each element 402, a relative position of at least one neighboring text element 414 using the absolute positions 408 recorded for each element 402. Using these relative positions, elements that are arranged in rows and columns will be apparent.

Next, a header 416 is located, the header 416 being a row 418 or column 420 that contains labeling information for a portion of the table 410. The header 416 may be located by comparing the content of the potential table entries along the borders with the content in the center, according to some embodiments.

Once a potential header 416 is located, it may be confirmed by validating the content of at least one element in the row or column represented by the header element. For example, if the potential header element has the content "Cost", validation may determine if the elements represented by that header element conform to the validation criteria 220 of the data detector 200 for that particular "Cost".

Upon validation of the header and the data it represents, the remaining validated elements 402 of the table 410 are associated with the various data detectors 200 that are appropriate for that particular data type (e.g. the detectors 200 used to identify and validate the header elements, etc.).

Next, the remaining elements 402 (i.e. the elements that are not in any tables 410) are examined by first identifying a potential descriptor 308 (i.e. a potential label 306) by comparing the element content with various data detectors. Upon finding a potential descriptor 308, it is determined if the element pointed to by one of the at least one direction 216 of the data detector 200 used to identify the potential descriptor 308 meets the validation criteria 220 of the data detector 200. See circle '7'. The validated text elements 402 are then associated with the various appropriate data detectors 200, meaning their content is noted to be of the data type represented by that data detector used to validate.

Next, in some embodiments, the content 404 of the validated text elements 402 are stored in the database 104, organized into a document record 236 according to the associations made with the data detectors 200. See circle '8'. Finally, for each data detector 200 that matched, the history 226 associated with the source (i.e. source 230) is updated according to which identifier 204 and/or direction 216 matched the most text elements of that data type 202 in the document 108. See circle '9'. This advantageously allows the system 100 to continue to operate with efficiency and agility, able to adapt to a change in document format from that source 230 after a single ingestion, without being stymied by the new formatting like most conventional systems.

Figure 5:
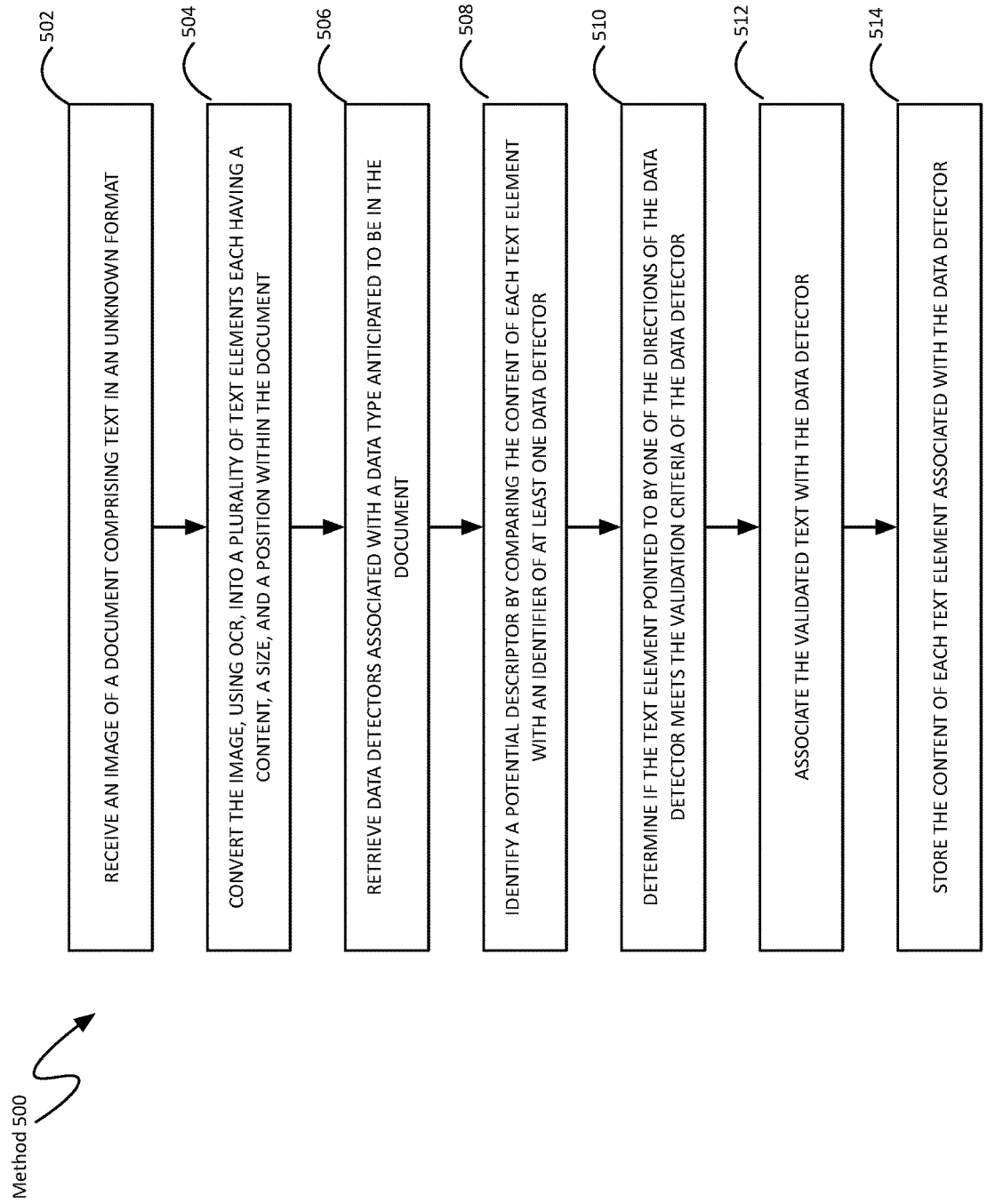
FIG. 5 is a process flow for a method for format-agnostic document ingestion.

FIG. 5 is a process flow for a non-limiting example of a method for format-agnostic document ingestion. As shown, the method 500 includes receiving, by a processor, an image of a document, the document comprising text arranged in an unknown format (step 502), and then converting (step 504), using optical character recognition performed by the processor, the image of the document into a plurality of text elements, each text element comprising a content, a size, and an absolute position within the document.

In some embodiments, the server retrieves a plurality of data detectors, each data detector associated with a data type that is anticipated to be in the document, each data detector comprising at least one identifier that is a potential label, at least one direction describing a potential relative direction of a text element having a label associated with the data detector, and at least one validation criteria, wherein each validation criteria describes a valid format (step 506).

The method 500 further includes identifying a potential descriptor (e.g. data label) by comparing the content of each text element with the at least one identifier of at least one data detector (step 508). It is then determined if the text element pointed to by one of the at least one direction of the data detector used to identify the potential descriptor meets the validation criteria of the data detector (step 510). Finally, the method includes associating the validated text element with the data detector (step 512) and storing, for each text element associated with one data detector of the plurality of data detector, the content of the text element (step 514). In some embodiments, the content may be stored in a database, while in others it may be stored in a different form of electronic storage, or even transmitted over a network.

Applications for the systems and methods contemplated herein span across a number of different industries including, but not limited to, data science (e.g. automated creation of training data sets for AI/ML models, etc.), accounting and finance (e.g. the ingestion and sorting of a number of tax related documents such as receipts, invoices, manifests, and the like, etc.), retail (e.g. consolidation of wine tech sheets having a highly variable format with non-standard content, etc.), and healthcare (e.g. management of bills and insurance claims, etc.).

In some embodiments, the systems and methods contemplated herein may be used to allow one party interface with the legacy system of another, or interface a legacy system with a bleeding edge system, using these methods to bridge the gap in data and document formats between the different parties involved.

Figure 6:
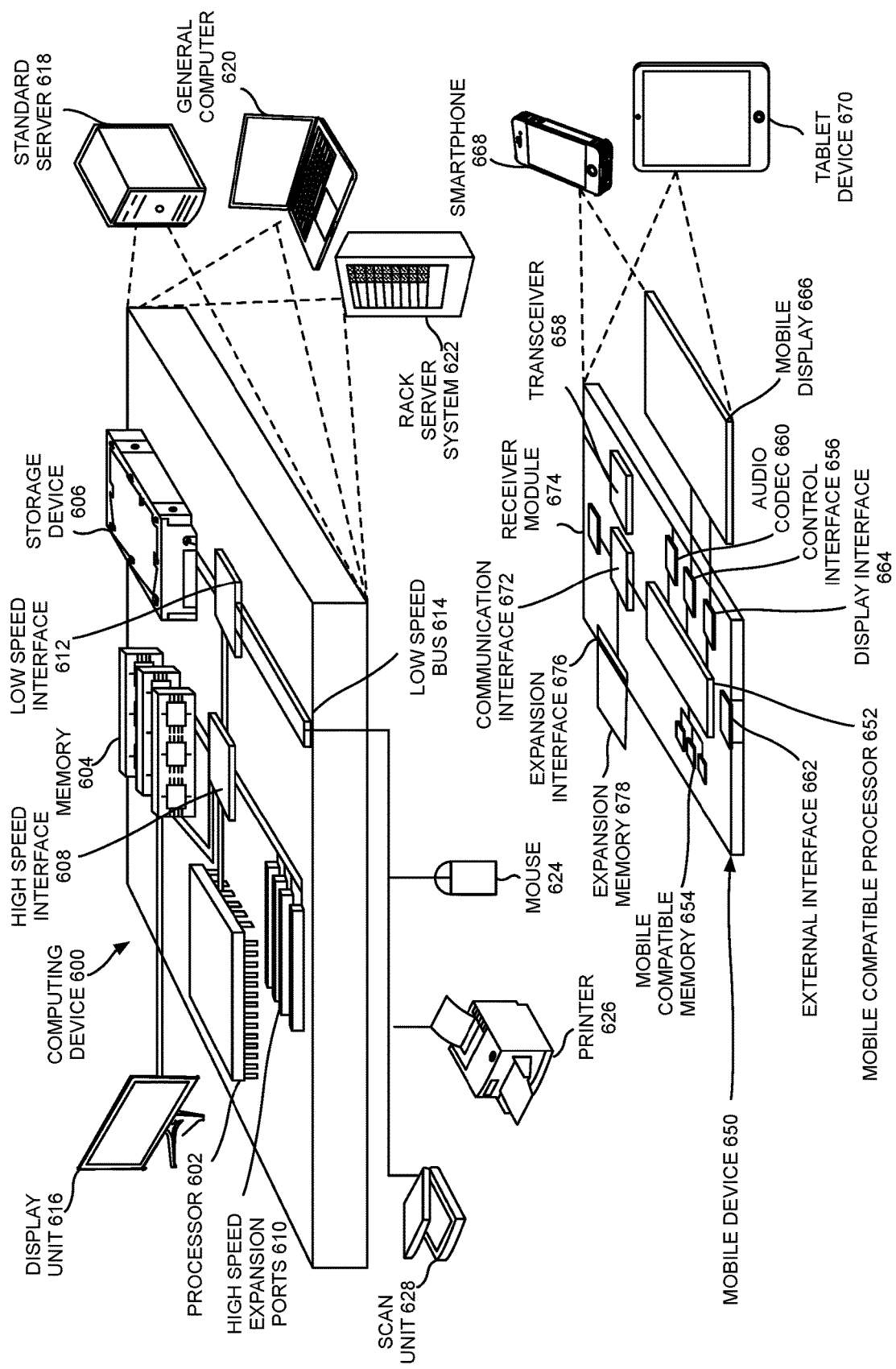
FIG. 6 is a schematic view of a specific computing device that can be used to implement the methods and systems disclosed herein.

FIG. 6 is a schematic diagram of specific computing device 600 and a specific mobile computing device 650 that can be used to perform and/or implement any of the embodiments disclosed herein. In one or more embodiments, document ingestion server 102, production server 112, database 104, third party server 110, client device 122 and/or capture device 116 of FIG. 1 may be the specific computing device 600. Furthermore, in one or more embodiments, client device 122, and/or capture device 116 of FIG. 1 may be the specific mobile computing device 650.

The specific computing device 600 may represent various forms of digital computers, such as laptops, desktops, workstations, personal digital assistants, servers, blade servers, mainframes, and/or other appropriate computers. The specific mobile computing device 650 may represent various forms of mobile devices, such as smartphones, camera phones, personal digital assistants, cellular telephones, and other similar mobile devices. The components shown here, their connections, couples, and relationships, and their functions, are meant to be exemplary only, and are not meant to limit the embodiments described and/or claimed, according to one embodiment.

The specific computing device 600 may include a processor 602, a memory 604, a storage device 606, a high speed interface 608 coupled to the memory 604 and a plurality of high speed expansion ports 610, and a low speed interface 612 coupled to a low speed bus 614 and a storage device 606. In one embodiment, each of the components heretofore may be inter-coupled using various buses, and may be mounted on a common motherboard and/or in other manners as appropriate. The processor 602 may process instructions for execution in the specific computing device 600, including instructions stored in the memory 604 and/or on the storage device 606 to display a graphical information for a GUI on an external input/output device, such as a display unit 616 coupled to the high speed interface 608, according to one embodiment.

In other embodiments, multiple processors and/or multiple buses may be used, as appropriate, along with multiple memories and/or types of memory. Also, a plurality of specific computing device 600 may be coupled with, with each device providing portions of the necessary operations (e.g., as a server bank, a group of blade servers, and/or a multi-processor system).

The memory 604 may be coupled to the specific computing device 600. In one embodiment, the memory 604 may be a volatile memory. In another embodiment, the memory 604 may be a non-volatile memory. The memory 604 may also be another form of computer-readable medium, such as a magnetic and/or an optical disk. The storage device 606 may be capable of providing mass storage for the specific computing device 600. In one embodiment, the storage device 606 may be includes a floppy disk device, a hard disk device, an optical disk device, a tape device, a flash memory and/or other similar solid state memory device. In another embodiment, the storage device 606 may be an array of the devices in a computer-readable medium previously mentioned heretofore, computer-readable medium, such as, and/or an array of devices, including devices in a storage area network and/or other configurations.

A computer program may be comprised of instructions that, when executed, perform one or more methods, such as those described above. The instructions may be stored in the memory 604, the storage device 606, a memory coupled to the processor 602, and/or a propagated signal.

The high speed interface 608 may manage bandwidth-intensive operations for the specific computing device 600, while the low speed interface 612 may manage lower bandwidth-intensive operations. Such allocation of functions is exemplary only. In one embodiment, the high speed interface 608 may be coupled to the memory 604, the display unit 616 (e.g., through a graphics processor and/or an accelerator), and to the plurality of high speed expansion ports 610, which may accept various expansion cards.

In the embodiment, the low speed interface 612 may be coupled to the storage device 606 and the low speed bus 614. The low speed bus 614 may be comprised of a wired and/or wireless communication port (e.g., a Universal Serial Bus ("USB"), a Bluetooth® port, an Ethernet port, and/or a wireless Ethernet port). The low speed bus 614 may also be coupled to the scan unit 628, a printer 626, a keyboard, a mouse 624, and a networking device (e.g., a switch and/or a router) through a network adapter.

The specific computing device 600 may be implemented in a number of different forms, as shown in the figure. In one embodiment, the specific computing device 600 may be implemented as a standard server 618 and/or a group of such servers. In another embodiment, the specific computing device 600 may be implemented as part of a rack server system 622. In yet another embodiment, the specific computing device 600 may be implemented as a general computer 620 such as a laptop or desktop computer. Alternatively, a component from the specific computing device 600 may be combined with another component in a specific mobile computing device 650. In one or more embodiments, an entire system may be made up of a plurality of specific computing device 600 and/or a plurality of specific computing device 600 coupled to a plurality of specific mobile computing device 650.

In one embodiment, the specific mobile computing device 650 may include a mobile compatible processor 652, a mobile compatible memory 654, and an input/output device such as a mobile display 666, a communication interface 672, and a transceiver 658, among other components. The specific mobile computing device 650 may also be provided with a storage device, such as a microdrive or other device, to provide additional storage. In one embodiment, the components indicated heretofore are inter-coupled using various buses, and several of the components may be mounted on a common motherboard.

The mobile compatible processor 652 may execute instructions in the specific mobile computing device 650, including instructions stored in the mobile compatible memory 654. The mobile compatible processor 652 may be implemented as a chipset of chips that include separate and multiple analog and digital processors. The mobile compatible processor 652 may provide, for example, for coordination of the other components of the specific mobile computing device 650, such as control of user interfaces, applications run by the specific mobile computing device 650, and wireless communication by the specific mobile computing device 650.

The mobile compatible processor 652 may communicate with a user through the control interface 656 and the display interface 664 coupled to a mobile display 666. In one embodiment, the mobile display 666 may be a Thin-Film-Transistor Liquid Crystal Display ("TFT LCD"), an Organic Light Emitting Diode ("OLED") display, and another appropriate display technology. The display interface 664 may comprise appropriate circuitry for driving the mobile display 666 to present graphical and other information to a user. The control interface 656 may receive commands from a user and convert them for submission to the mobile compatible processor 652.

In addition, an external interface 662 may be provide in communication with the mobile compatible processor 652, so as to enable near area communication of the specific mobile computing device 650 with other devices. External interface 662 may provide, for example, for wired communication in some embodiments, or for wireless communication in other embodiments, and multiple interfaces may also be used.

The mobile compatible memory 654 may be coupled to the specific mobile computing device 650. The mobile compatible memory 654 may be implemented as a volatile memory and a non-volatile memory. The expansion memory 678 may also be coupled to the specific mobile computing device 650 through the expansion interface 676, which may comprise, for example, a Single In Line Memory Module ("SIMM") card interface. The expansion memory 678 may provide extra storage space for the specific mobile computing device 650, or may also store an application or other information for the specific mobile computing device 650.

Specifically, the expansion memory 678 may comprise instructions to carry out the processes described above. The expansion memory 678 may also comprise secure information. For example, the expansion memory 678 may be provided as a security module for the specific mobile computing device 650, and may be programmed with instructions that permit secure use of the specific mobile computing device 650. In addition, a secure application may be provided on the SIMM card, along with additional information, such as placing identifying information on the SIMM card in a non-hackable manner.

The mobile compatible memory may include a volatile memory (e.g., a flash memory) and a non-volatile memory (e.g., a non-volatile random-access memory ("NVRAM")). In one embodiment, a computer program comprises a set of instructions that, when executed, perform one or more methods. The set of instructions may be stored on the mobile compatible memory 654, the expansion memory 678, a memory coupled to the mobile compatible processor 652, and a propagated signal that may be received, for example, over the transceiver 658 and/or the external interface 662.

The specific mobile computing device 650 may communicate wirelessly through the communication interface 672, which may be comprised of a digital signal processing circuitry. The communication interface 672 may provide for communications using various modes and/or protocols, such as, a Global System for Mobile Communications ("GSM") protocol, a Short Message Service ("SMS") protocol, an Enhanced Messaging System ("EMS") protocol, a Multimedia Messaging Service ("MMS") protocol, a Code Division Multiple Access ("CDMA") protocol, Time Division Multiple Access ("TDMA") protocol, a Personal Digital Cellular ("PDC") protocol, a Wideband Code Division Multiple Access ("WCDMA") protocol, a CDMA2000 protocol, and a General Packet Radio Service ("GPRS") protocol.

Such communication may occur, for example, through the transceiver 658 (e.g., radio-frequency transceiver). In addition, short-range communication may occur, such as using a Bluetooth®, Wi-Fi, and/or other such transceiver. In addition, a GPS ("Global Positioning System") receiver module 674 may provide additional navigation-related and location-related wireless data to the specific mobile computing device 650, which may be used as appropriate by a software application running on the specific mobile computing device 650.

The specific mobile computing device 650 may also communicate audibly using an audio codec 660, which may receive spoken information from a user and convert it to usable digital information. The audio codec 660 may likewise generate audible sound for a user, such as through a speaker (e.g., in a handset smartphone of the specific mobile computing device 650). Such a sound may comprise a sound from a voice telephone call, a recorded sound (e.g., a voice message, a music files, etc.) and may also include a sound generated by an application operating on the specific mobile computing device 650.

The specific mobile computing device 650 may be implemented in a number of different forms, as shown in the figure. In one embodiment, the specific mobile computing device 650 may be implemented as a smartphone 668. In another embodiment, the specific mobile computing device 650 may be implemented as a personal digital assistant ("PDA"). In yet another embodiment, the specific mobile computing device, 650 may be implemented as a tablet device 670.

Various embodiments of the systems and techniques described here can be realized in a digital electronic circuitry, an integrated circuitry, a specially designed application specific integrated circuits ("ASICs"), a piece of computer hardware, a firmware, a software application, and a combination thereof. These various embodiments can include embodiment in one or more computer programs that are executable and/or interpretable on a programmable system including one programmable processor, which may be special or general purpose, coupled to receive data and instructions from, and to transmit data and instructions to, a storage system, one input device, and at least one output device.

These computer programs (also known as programs, software, software applications, and/or code) comprise machine-readable instructions for a programmable processor, and can be implemented in a high-level procedural and/or object-oriented programming language, and/or in assembly/machine language. As used herein, the terms "machine-readable medium" and/or "computer-readable medium" refers to any computer program product, apparatus and/or device (e.g., magnetic discs, optical disks, memory, and/or Programmable Logic Devices ("PLDs")) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here may be implemented on a computing device having a display device (e.g., a cathode ray tube ("CRT") and/or liquid crystal ("LCD") monitor) for displaying information to the user and a keyboard and a mouse by which the user can provide input to the computer. Other kinds of devices can be used to provide for interaction with a user as well; for example, feedback provided to the user can be any form of sensory feedback (e.g., visual feedback, auditory feedback, and/or tactile feedback) and input from the user can be received in any form, including acoustic, speech, and/or tactile input.

The systems and techniques described here may be implemented in a computing system that includes a back end component (e.g., as a data server), a middleware component (e.g., an application server), a front end component (e.g., a client computer having a graphical user interface, and/or a Web browser through which a user can interact with an embodiment of the systems and techniques described here), and a combination thereof. The components of the system may also be coupled through a communication network.

The communication network may include a local area network ("LAN") and a wide area network ("WAN") (e.g., the Internet). The computing system can include a client and a server. In one embodiment, the client and the server are remote from each other and interact through the communication network.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

Where the above examples, embodiments and implementations reference examples, it should be understood by those of ordinary skill in the art that other document ingestion systems and methods could be intermixed or substituted with those provided. In places where the description above refers to particular embodiments of format-agnostic document ingestion systems and methods, it should be readily apparent that a number of modifications may be made without departing from the spirit thereof and that these embodiments and implementations may be applied to other to document digitization systems and methods as well. Accordingly, the disclosed subject matter is intended to embrace all such alterations, modifications and variations that fall within the spirit and scope of the disclosure and the knowledge of one of ordinary skill in the art.

What is claimed is:

1. A system for format-agnostic document ingestion, comprising:
    a document ingestion server comprising a processor and a memory, the document ingestion server communicatively coupled to a database, the processor configured to:
        receive an image of a document, the document comprising text arranged in an unknown format;
        convert, using optical character recognition, the image of the document into a plurality of text elements, each text element comprising a content, a size, and an absolute position within the document;
        identify a document type by searching the content of each text element for a plurality of distinguishing strings, each distinguishing string being unique to one document type;
        retrieve a plurality of data detectors from the database based on the document type, each data detector associated with a data type that is anticipated to be in the document, each data detector comprising at least one identifier that is one of a potential label and a potential format, at least one direction describing a potential relative direction of a text element having a label associated with the data detector, and at least one validation criteria, wherein each validation criteria describes one of a valid format and a valid range;
        determine a source of the document by comparing the at least one identifier of a data detector associated with a data type that is unique among potential document sources with the content of each text element of the plurality of text elements;
        for each data detector, order at least one of the identifiers and the directions according to a history stored in the database and associated with the source;
        identify a table within the document by calculating for each text element of the plurality of text elements a relative position of at least one neighboring text element relative to the text element using the absolute position of the text element, and comparing the relative positions of the plurality of text elements;
        locate a header for the table by comparing the content of the text elements within the table with the identifiers of the plurality of data detectors and then identifying the data type of the matching text elements, the header being one of a row and a column;
        validate, for each identified text element in the header, at least one text element within the other of a row and a column described by the identified text element in the header with the validation criteria of the data detector that identified the identified text element in the header;
        associate, for each identified text element in the header, at least one validated text element within the other of the row and the column described by the identified text element in the header with the data detector that identified the identified text element in the header;

identify a potential descriptor by comparing the content of each text element not part of the table with the at least one identifier of at least one data detector;

determine if the text element pointed to by one of the at least one direction of the data detector used to identify the potential descriptor meets the validation criteria of the data detector;

associate the validated text element with the data detector;

store, for each text element associated with one data detector of the plurality of data detector, the content of the text element, in the database; and update, for each data detector, the history associated with the source, according to which identifier of the at least one identifier and which direction of the at least one direction matched the most text elements of the data type described by the data detector in the document.

2. The system of claim 1, wherein the processor is further configured to:
train a machine learning model correlating text elements with the data detectors they have been associated with;
determine whether the machine learning model performs better than one or more data detectors; and
automatically employ the machine learning model in place of the one or more data detectors once the machine learning model outperforms the one or more data detectors.

3. The system of claim 1, wherein determining the source of the document comprises identifying all postal addresses in the document based upon an observed format, validating each postal address, placing each postal address in a standard format, and comparing each address with a list of addresses unique to each of a plurality of known document sources.

4. The system of claim 1, wherein each text element further comprises a size, and wherein the potential format of each data detector further comprises a potential size.

5. A system for format-agnostic document ingestion, comprising:
a document ingestion server comprising a processor and a memory, the document ingestion server communicatively coupled to a database, the processor configured to:
receive an image of a document, the document comprising text arranged in an unknown format;
convert, using optical character recognition, the image of the document into a plurality of text elements, each text element comprising a content, a size, and an absolute position within the document;
retrieve a plurality of data detectors from the database, each data detector associated with a data type that is anticipated to be in the document, each data detector comprising at least one identifier that is a potential label, at least one direction describing a potential relative direction of a text element having a label associated with the data detector, and at least one validation criteria, wherein each validation criteria describes a valid format;
identify a potential descriptor by comparing the content of each text element with the at least one identifier of at least one data detector;
determine if the text element pointed to by one of the at least one direction of the data detector used to identify the potential descriptor meets the validation criteria of the data detector;

associate the validated text element with the data detector; and store, for each text element associated with one data detector of the plurality of data detector, the content of the text element, in the database, and wherein the processor is further configured to:
determine a source of the document by comparing the at least one identifier of a data detector associated with a data type that is unique among potential document sources with the content of each text element of the plurality of text elements; and for each data detector, order at least one of the identifiers and the directions according to a history stored in the database and associated with the source; and update, for each data detector, the history associated with the source, according to which identifier of the at least one identifier and which direction of the at least one direction matched the most text elements of the data type described by the data detector in the document.

6. The system of claim 5:
wherein the processor is further configured to identify a document type by searching the content of each text element for a plurality of distinguishing strings, each distinguishing string being unique to one document type; and
wherein the plurality of data detectors retrieved from the database is selected based on the document type.

7. The system of claim 5, wherein each identifier is at least one of a potential label and a potential format.

8. The system of claim 5, wherein each validation criteria describes at least one of a valid format and a valid range.

9. The system of claim 5, wherein the processor is further configured to:
identify a table within the document by calculating for each text element of the plurality of text elements a relative position of at least one neighboring text element relative to the text element using the absolute position of the text element, and comparing the relative positions of the plurality of text elements;

locate a header for the table by comparing the content of the text elements within the table with the identifiers of the plurality of data detectors and then identifying the data type of the matching text elements, the header being one of a row and a column;

validate, for each identified text element in the header, at least one text element within the other of a row and a column described by the identified text element in the header with the validation criteria of the data detector that identified the identified text element in the header; and associate, for each identified text element in the header, at least one validated text element within the other of the row and the column described by the identified text element in the header with the data detector that identified the identified text element in the header.

10. The system of claim 5, wherein the processor is further configured to:
train a machine learning model correlating text elements with the data detectors they have been associated with;
determine whether the machine learning model performs better than one or more data detectors; and
automatically employ the machine learning model in place of the one or more data detectors once the machine learning model outperforms the one or more data detectors.

11. The system of claim 5, wherein determining the source of the document comprises identifying all postal addresses in the document based upon an observed format, validating each postal address, placing each postal address in a standard format, and comparing each address with a list of addresses unique to each of a plurality of known document sources.

12. A method for format-agnostic document ingestion, comprising:
- receiving, by a processor, an image of a document, the document comprising text arranged in an unknown format;
- converting, using optical character recognition performed by the processor, the image of the document into a plurality of text elements, each text element comprising a content, a size, and an absolute position within the document;
- retrieving a plurality of data detectors, each data detector associated with a data type that is anticipated to be in the document, each data detector comprising at least one identifier that is a potential label, at least one direction describing a potential relative direction of a text element having a label associated with the data detector, and at least one validation criteria, wherein each validation criteria describes a valid format,
- identifying a potential descriptor by comparing the content of each text element with the at least one identifier of at least one data detector;
- determining if the text element pointed to by one of the at least one direction of the data detector used to identify the potential descriptor meets the validation criteria of the data detector;
- associating the validated text element with the data detector; and
- storing, for each text element associated with one data detector of the plurality of data detector, the content of the text element; and further comprising
- determining a source of the document by comparing the at least one identifier of a data detector associated with a data type that is unique among potential document sources with the content of each text element of the plurality of text elements; and
- ordering, for each data detector, at least one of the identifiers and the directions according to a history associated with the source; and
- updating, for each data detector, the history associated with the source, according to which identifier of the at least one identifier and which direction of the at least one direction matched the most text elements of the data type described by the data detector in the document.

13. The method of claim 12, further comprising:
- identifying a document type by searching the content of each text element for a plurality of distinguishing strings, each distinguishing string being unique to one document type;
- wherein the plurality of data detectors retrieved is selected based on the document type.

14. The method of claim 12, wherein each identifier is one of a potential label and a potential format.

15. The method of claim 12, wherein each validation criteria describes one of a valid format and a valid range.

16. The method of claim 12, further comprising:
- identifying a table within the document by calculating for each text element of the plurality of text elements a relative position of at least one neighboring text element relative to the text element using the absolute position of the text element, and comparing the relative positions of the plurality of text elements;
- locating a header for the table by comparing the content of the text elements within the table with the identifiers of the plurality of data detectors and then identifying the data type of the matching text elements, the header being one of a row and a column;
- validating, for each identified text element in the header, at least one text element within the other of a row and a column described by the identified text element in the header with the validation criteria of the data detector that identified the identified text element in the header; and
- associating, for each identified text element in the header, at least one validated text element within the other of the row and the column described by the identified text element in the header with the data detector that identified the identified text element in the header.

17. The method of claim 12, further comprising:
- training a machine learning model correlating text elements with the data detectors they have been associated with;
- determining whether the machine learning model performs better than one or more data detectors; and
- automatically employ the machine learning model in place of the one or more data detectors once the machine learning model outperforms the one or more data detectors.

18. The method of claim 12, wherein determining the source of the document comprises identifying all postal addresses in the document based upon an observed format, validating each postal address, placing each postal address in a standard format, and comparing each address with a list of addresses unique to each of a plurality of known document sources.

* * * * *